United States Patent [19]

Hirabayashi et al.

[11] Patent Number: 5,436,225

[45] Date of Patent: Jul. 25, 1995

[54] PLANT GROWTH REGULATOR COMPOSITION COMPRISING A CYCLOHEXANONE COMPOUND AND ADJUVANTS

[75] Inventors: Yoshinori Hirabayashi, Shizuoka; Toshihiro Ikeuchi, Shimizu; Susumu Kato; Takeshige Miyazawa, both of Shizuoka; Kanji Nakamura, Shimizu, all of Japan

[73] Assignee: Kumiai Chemical Industry Co., Ltd., Tokyo, Japan

[21] Appl. No.: 152,132

[22] Filed: Nov. 16, 1993

[30] Foreign Application Priority Data

Nov. 19, 1992 [JP] Japan ................ 4-332221

[51] Int. Cl.$^6$ .................. A01N 43/10; A01N 37/08; A01N 35/06; A01N 25/30
[52] U.S. Cl. .................. 504/289; 504/313; 504/317; 504/319; 504/320; 504/321; 504/325; 71/DIG. 1
[58] Field of Search ............. 504/320, 289, 313, 317, 504/319, 321, 325; 71/DIG. 1

[56] References Cited

U.S. PATENT DOCUMENTS

| | | | |
|---|---|---|---|
| 4,581,057 | 4/1986 | Nooden | 71/28 |
| 4,678,496 | 7/1987 | Motojima et al. | 71/76 |
| 5,154,753 | 10/1992 | Meyer et al. | 71/121 |

FOREIGN PATENT DOCUMENTS

| | | |
|---|---|---|
| 0114960 | 8/1984 | European Pat. Off. . |
| 0224441 | 6/1987 | European Pat. Off. . |
| 0320864 | 6/1989 | European Pat. Off. . |
| 0338986 | 10/1989 | European Pat. Off. . |
| 0344533 | 12/1989 | European Pat. Off. . |
| 0434613 | 6/1991 | European Pat. Off. . |

*Primary Examiner*—S. Mark Clardy
*Attorney, Agent, or Firm*—Oblon, Spivak, McClelland, Maier & Neustadt

[57] ABSTRACT

A plant growth regulator composition comprising a cyclohexane derivative of the formula:

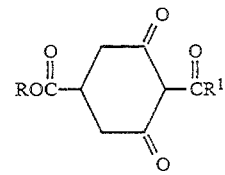

wherein R is a hydrogen atom, a lower alkyl group, an alkylthioalkyl group, a phenyl group or a substituted phenyl group, and $R^1$ is a lower alkyl group, a cycloalkyl group, a benzyl group, a substituted benzyl group, a phenethyl group, a phenoxymethyl group, a 2-thienylmethyl group, an alkoxymethyl group or an alkylthiomethyl group, or a salt thereof, and a nitrogen-containing water-soluble inorganic substance or urea.

9 Claims, No Drawings

PLANT GROWTH REGULATOR COMPOSITION COMPRISING A CYCLOHEXANONE COMPOUND AND ADJUVANTS

The present invention relates to a plant growth regulator composition comprising a cyclohexane derivative or its salt and a nitrogen-containing water-soluble inorganic substance or urea, which may further contain a polyoxyethylene alkyl ether, a polyoxyethylene alkyl phenyl ether, a mineral oil or a vegetable oil.

In the field of so-called chemical control to regulate the growth of a plant by a chemical substance, maleic hydrazide, daminozide (N,N-dimethylamino succinimide), mepiquat chloride (1,1-dimethylpiperidinium chloride) or chlormequat chloride (2-chloroethyl trimethylammonium chloride) has been used for the purpose of controlling the growth of a plant, controlling germination of lateral buds or preventing lodging of a plant. However, each of such compounds had various drawbacks such that the applicable site, the applicable plants and the applicable period of time were limited, the effects were instable, and a phytotoxicity was brought about. Recently, various cyclohexane derivatives or their salts have been developed as plant growth regulators (Japanese Unexamined Patent Publications No. 164543/1983, No. 196840/1984 and No. 231045/1984). However, these compounds also have difficulties such that when applied in a low dose, the effects tend to be unstable depending upon the objective plants, and the residual effects are sometimes inadequate.

Further, it is known to incorporate ammonium sulfate or urea to a herbicide 2-amino-4-[(hydroxy)(methyl)-phosphinoyl]butyric acid (Japanese Unexamined Patent Publication No. 18311/1983) or to glyphosate (Japanese Unexamined Patent Publications No. 145205/1988 and No. 34901/1991). However, it is not known to incorporate it to a cyclohexane derivative as a plant growth regulator.

It is likely that an agricultural chemical is applied in an excess amount to obtain adequate effects. However, it is not desirable to apply a large amount of such a chemical from the viewpoint of possible dangers to the safety of animals and human being, environmental pollution or economical load to the farmer. Therefore, it has been desired to develop an agricultural composition which exhibits adequate effects with a small amount and which is free from a phytotoxicity to crop plants. The present inventors have conducted extensive researches to improve the persistency of the plant growth regulating effects of a cyclohexane derivative or its salt and to stabilize the effects when it is applied at a low dose. As a result, they have found that it is possible to obtain a plant growth regulator composition having extremely high effects by incorporating a nitrogen-containing water-soluble inorganic substance or urea to a composition of a cyclohexane derivative or its salt, and it is further possible to obtain further stabilized plant growth regulating effects at a low dose in combination with the action of the above nitrogen-containing water-soluble inorganic substance by incorporating one or more members selected from the group consisting of polyoxyethylene alkyl ethers, polyoxyethylene alkylphenyl ethers, mineral oils and vegetable oils, to the plant growth regulator composition. The present invention has been accomplished on the basis of these discoveries.

Thus, the present invention provides a plant growth regulator composition comprising a cyclohexane derivative of the formula:

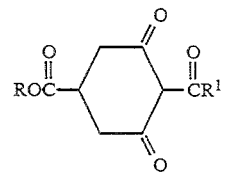

wherein R is a hydrogen atom, a lower alkyl group, an alkylthioalkyl group, a phenyl group or a substituted phenyl group, and $R^1$ is a lower alkyl group, a cycloalkyl group, a benzyl group, a substituted benzyl group, a phenethyl group, a phenoxymethyl group, a 2-thienylmethyl group, an alkoxymethyl group or an alkylthiomethyl group, or a salt thereof, and a nitrogen-containing water-soluble inorganic substance or urea.

Further, the plant growth regulator composition of the present invention preferably contains, in addition to the above components, one or more members selected from the group consisting of polyoxyethylene alkyl ethers, polyoxyethylene alkylphenyl ethers, mineral oils and vegetable oils.

In the present invention, the salt of the cyclohexane derivative may be of the formula:

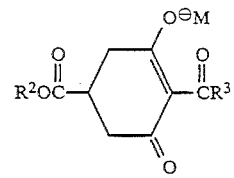

wherein M is an organic or inorganic cation, $R^2$ is a hydrogen atom or a lower alkyl group, and $R^3$ is a lower alkyl group,

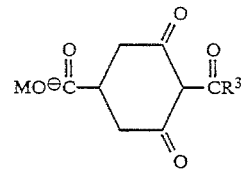

wherein M is an organic or inorganic cation, and $R^3$ is a lower alkyl group, or

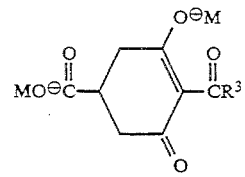

wherein M is an organic or inorganic cation, and $R^3$ is a lower alkyl group.

In the present invention, the substituted phenyl group and the substituted benzyl group may be those substituted by a halogen atom, an alkyl group (having from 1 to 5 carbon atoms) or an alkoxy group (having from 1 to 5 carbon atoms). The organic or inorganic cation may, for example, be a cation such as an alkali metal, an alkaline earth metal, a mono-, di- or tri-alkyl ammonium, a dialkali (substituted benzyl)ammonium, or a mono- or bis-(hydroxyethyl)ammonium.

Specific examples of the cyclohexane derivative and its salt will be shown in Tables 1 to 4, but the cyclohexane derivatives and its salt are not limited to such specific examples.

TABLE 1

| Compound No. | R | R¹ |
|---|---|---|
| 1 | $C_2H_5$ | $C_2H_5$ |
| 2 | $C_2H_5$ |  |
| 3 | $CH_3$ | 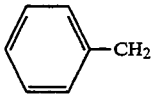 |
| 4 | $C_2H_5$ | 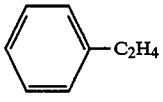 |
| 5 | $C_2H_5$ | 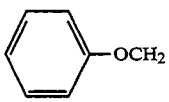 |
| 6 | $C_2H_5$ | 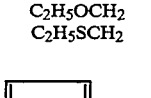 |
| 7 | $C_2H_5$ | $C_2H_5OCH_2$ |
| 8 | $C_2H_5$ | $C_2H_5SCH_2$ |
| 9 | $C_2H_5$ | 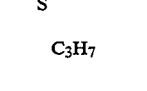 |
| 10 | $CH_3SC_2H_4$ | $C_3H_7$ |
| 11 | $C_2H_5$ | 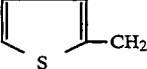 |
| 12 | 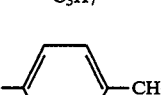 | $C_3H_7$ |
| 13 | 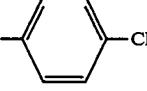 | $C_3H_7$ |

TABLE 2

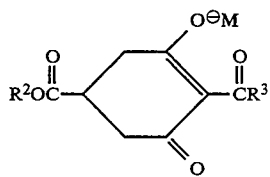

| Compound No. | R² | R³ | M |
|---|---|---|---|
| 14 | $CH_3$ | $CH_3$ | $H_2N^{\oplus}(C_2H_4OH)_2$ |
| 15 | $C_2H_5$ | $CH_3$ | $H_2N^{\oplus}(C_2H_5)_2$ |
| 16 | $C_2H_5$ | $C_2H_5$ | $H_2N^{\oplus}(C_2H_4OH)_2$ |

TABLE 3

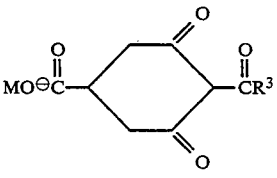

| Compound No. | R³ | M |
|---|---|---|
| 17 | $C_3H_7$ | $HN^{\oplus}(C_2H_5)_3$ |
| 18 | $C_2H_5$ | 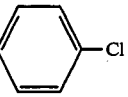 |
| 19 | $C_2H_5$ | $Na^{\oplus}$ |

TABLE 4

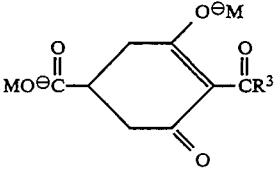

| Compound No. | R³ | M |
|---|---|---|
| 20 | $C_2H_5$ | $\frac{1}{2}Ca^{\oplus\oplus}$ |
| 21 | $C_2H_5$ | $Na^{\oplus}$ |
| 22 | $C_2H_5$ | $H_2N^{\oplus}(C_2H_4OH)_2$ |

In the present invention, the nitrogen-containing water-soluble inorganic substance may, for example, be a solid ammonium salt substance or a nitrate substance. Among them, ammonium sulfate, ammonium nitrate, ammonium chloride, ammonium phosphate, sodium nitrate and potassium nitrate are preferred. These inorganic substances may be used alone or in combination as a mixture of two or more of them.

In the present invention, the ratio of the cyclohexane derivative or its salt to the nitrogen-containing water-soluble inorganic substance or urea, varies depending upon the active ingredient, the type of the formulation, the carrier, the surfactant, etc. However, it is preferable such that the nitrogen-containing water-soluble inorganic substance or urea is within a range of from 0.2 to 1000 parts by weight, preferably from 0.5 to 100 parts by weight, per part by weight of the cyclohexane derivative or its salt.

In the case of a formulation which is applied by itself, such as a dust or granule, the nitrogen-containing water-soluble inorganic substance or urea is usually used in an amount of from 2 to 10 times the amount used for a formulation to be used as diluted with water, such as a wettable powder, a granular wettable powder or a flowable. Namely, in the case of a formulation to be used as diluted with water, such as a wettable powder or a flowable, the ratio of the cyclohexane derivative or its salt to the nitrogen-containing water-soluble inorganic substance or urea is preferably from 1:0.5 to 1:10. Whereas, in the case of a formulation to be applied by itself, the ratio is preferably from 1:10 to 1:100.

Further, the content in the formulation of the cyclohexane derivative or its salt and the nitrogen-containing water-soluble inorganic substance or urea in the composition of the present invention, is usually from 0.1 to 99% by weight, preferably from 1.0 to 95% by weight, in the total amount of the two components, in the case of a wettable powder, a granular wettable powder and a flowable. It is usually from 0.01 to 20% by weight, preferably from 0.05 to 10% by weight, in the total amount of the two components, in the case of a dust.

The polyoxyethylene alkyl ethers and the polyoxyethylene alkylphenyl ethers to be used in the present invention, are preferably those in which the average addition molarity of ethylene oxide is from 2 to 16 mols, and the carbon number of the alkyl group is from 8 to 16 and which are non-ionic. For example, a polyoxyethylene lauryl ether (the average addition molarity of ethylene oxide: from 4 to 12 mols), a polyoxyethylene tridecyl ether (the average addition molarity of ethylene oxide: from 4 to 12 mols), a polyoxyethylene myristyl ether (the average addition molarity of ethylene oxide: from 4 to 12 mols), a polyoxyethylene octylphenyl ether (the average addition molarity of ethylene oxide: from 4 to 12 mols) and a polyoxyethylene nonylphenyl ether (the average addition molarity of ethylene oxide: from 4 to 12 mols), may be mentioned. Further, such polyoxyethylene alkyl ethers and polyoxyethylene alkylphenyl ethers may be used alone, or in combination as a mixture of two or more of them. Further, they may be used in combination with mineral oils or vegetable oils which will be described below.

The mineral oils or vegetable oils to be used in the present invention are those which have a dynamic viscosity within a range of from 1 to 300 cSt at 40° C. The mineral oils may be paraffinic hydrocarbons or naphthenic hydrocarbons, such as spindle oil, liquid paraffin, n-paraffin and machine oil. The vegetable oils may, for example, natural vegetable oils or purified products thereof, such as soybean oil, sunflower oil, rapeseed oil, corn oil, coconut oil, linseed oil, cotton oil, tung oil, castor oil, palm oil, olive oil and rice bran oil. These mineral oils or vegetable oils may be used alone or in combination as a mixture of two or more of them.

The ratio of the cyclohexane derivative or its salt to the polyoxyethylene alkyl ethers, polyoxyethylene alkylphenyl ethers, mineral oils or vegetable oils is usually from 1:0.2 to 1:50, preferably from 1:0.5 to 1:20, by weight.

As a preferred example, the composition of the present invention comprises an ethyl ester of 3,5-dioxo-4-propionylcyclohexane carboxylic acid or a calcium salt of 3,5-dioxo-4-propionylcyclohexane carboxylic acid, ammonium sulfate and a polyoxyethylene alkyl ether or a polyoxyethylene alkylphenyl ether in which the average addition molarity of ethylene oxide is from 2 to 16 mols and the carbon number of the alkyl group is from 8 to 16, preferably a polyoxyethylene lauryl ether, wherein the ratio of the ethyl ester or the calcium salt of the cyclohexane carboxylic acid, the ammonium sulfate and the polyoxyethylene alkyl ether or polyoxyethylene alkylphenyl ether is 1:0.5–100:0.5–20, by weight.

The plant growth regulator composition of the present invention may be formulated by incorporating a surfactant, a flocculating agent, a filler, an organic solvent, a binder, a thickener and other adjuvants which are commonly employed for the formulation of agricultural chemicals, as the case requires. The surfactant may, for example, be an anionic or nonionic surfactant such as an alkyl phosphoric acid ester, a polyalkylene glycol, a polyoxyethylene-polyoxypropylene block polymer, an alkylaryl sulfonate, a polyoxyethylene alkylaryl ether sulfate, lignin sulfonate or naphthalene sulfonate. The flocculating agent is incorporated to prevent scattering of fine powder particles, and an organic phosphoric acid compound is usually employed. The filler may, for example, be a mineral fine powder such as clay, DL clay having fine particles of less than 10 μm excluded in a specified range, diatomaceous earth or calcium carbonate, saccharides such as lactose or sucrose, a water-soluble filler such as sodium sulfate, or water. The organic solvent may, for example, be a glycol such as ethylene glycol, propylene glycol or polyethylene glycol. The binder or thickener may, for example, be α-starch, carboxymethyl cellulose, PVP (polyvinyl pyrrolidone) or xanthane gum. Further, said other adjuvants include, for example, fine silica powder, silicone, a metal salt of a higher fatty acid and a coloring agent.

The plant growth regulator composition of the present invention may be used in the form of a formulation which is common for an agricultural chemical. However, it is particularly preferred to use it in the form of a solid such as a wettable powder, a granular wettable powder or a dust, or in the form of a liquid dispersed in water or in oil, such as a flowable.

To prepare a wettable powder, the cyclohexane derivative or its salt may, for example, be uniformly mixed with the nitrogen-containing water-soluble inorganic substance or urea, if necessary, together with one or more members selected from the group consisting of polyoxyethylene alkyl ethers, polyoxyethylene alkylphenyl ethers, vegetable oils and mineral oils, fine silica powder, a surfactant, or a filler such as clay, diatomaceous earth or calcium carbonate, and if necessary, finely pulverized.

To prepare a granular wettable powder, the cyclohexane derivative or its salt and the nitrogen-containing water-soluble inorganic substance or urea, if necessary together with one or more members selected from the group consisting of polyoxyethylene alkyl ethers, polyoxyethylene alkylphenyl ethers, vegetable oils and mineral oils, a surfactant, a binder, or a filler such as clay, diatomaceous earth or calcium carbonate, and if necessary fine silica powder, are mixed, and the mixture is granulated by mixing and stirring while adding a small amount of water, followed by drying.

To prepare a dust, the nitrogen-containing water-soluble inorganic substance or urea and, if necessary, one or more members selected from the group consisting of polyoxyethylene alkyl ethers, polyoxyethylene alkylphenyl ethers, vegetable oils and mineral oils, fine silica powder, a flocculating agent, or a filler such as clay, diatomaceous earth or calcium carbonate, may, for example, be mixed to the cyclohexane derivative or its salt, followed by pulverization.

To prepare a flowable, the nitrogen-containing water-soluble inorganic substance or urea and, if necessary, one or more members selected from the group consisting of polyoxyethylene alkyl ethers, polyoxyethylene alkylphenyl ethers, vegetable oils and mineral oils, a surfactant, a thickener, an organic solvent, water or oil, or other adjuvants, may, for example, be mixed to the cyclohexane derivative or its salt, and if necessary, the mixture is pulverized.

When all components are soluble to one another, the composition may be formulated in the form of a liquid formulation.

The plant growth regulator composition of the present invention may be formulated into a mixture by incorporating a plant growth regulator other than the cyclohexane derivative or its salt, an insecticide or a fungicide. Such a plant growth regulator may, for example, be mepiquat chloride or chloromequat. The insecticide may, for example, be MEP, dimethyl vinphos, chloropyrifosmethyl, pyridafenthione, diazinone, dimethoate, acephate, BPMC, MTMC, ethofenprox or buploprofezin. The fungicide may, for example, be tricyclazole, isoprothiolane, fthalide, IBP, mepronil, flutolanil or pencycuron.

Now, the present invention will be described in further detail with reference to Examples and Test Examples. However, it should be understood that the present invention is by no means restricted by such specific Examples. In these Examples, "parts" means "parts by weight".

| EXAMPLE 1 Granular wettable powder | |
|---|---|
| Compound No. 1 | 10 parts |
| Ammonium sulfate | 70 parts |
| Condensation product of sodium naphthalene sulfonate (Demol N, trademark, manufactured by Kao Corporation) | 5 parts |
| Fine silica powder (Carplex #1120, trademark, manufactured by Shionogi & Co., Ltd.) | 5 parts |
| Sucrose | 5 parts |
| Clay | 5 parts |

The above components were uniformly mixed and pulverized, and while adding a small amount of water, the mixture was mixed and stirred for granulation, followed by drying to obtain a granular wettable powder.

| EXAMPLE 2 Granular wettable powder | |
|---|---|
| Compound No. 1 | 10 parts |
| Ammonium sulfate | 60 parts |
| Polyoxyethylene lauryl ether (Emulgen 108, trademark, manufactured by Kao Corporation, average addition molarity of ethylene oxide: 6) | 10 parts |
| Condensation product of sodium naphthalene sulfonate (as mentioned above) | 5 parts |
| Fine silica powder (as mentioned above) | 10 parts |
| Sucrose | 5 parts |

The above components were uniformly mixed and pulverized, and while adding a small amount of water, the mixture was mixed and stirred for granulation, followed by drying to obtain a granular wettable powder.

| EXAMPLE 3 Granular wettable powder | |
|---|---|
| Compound No. 20 | 10 parts |
| Ammonium sulfate | 60 parts |
| Polyoxyethylene lauryl ether (as mentioned above) | 10 parts |
| Condensation product of sodium naphthalene sulfonate (as mentioned above) | 5 parts |
| Fine silica powder (as mentioned above) | 5 parts |
| Sucrose | 5 parts |
| Clay | 5 parts |

The above components were uniformly mixed and then pulverized, and while adding a small amount of water, the mixture was mixed and stirred for granulation, followed by drying to obtain a granular wettable powder.

| EXAMPLE 4 Granular wettable powder | |
|---|---|
| Compound No. 20 | 5 parts |
| Mepiquat-chloride | 30 parts |
| Ammonium sulfate | 25 parts |
| Polyoxyethylene lauryl ether (as mentioned above) | 5 parts |
| Condensation product of sodium naphthalene sulfonate (as mentioned above) | 5 parts |
| Fine silica powder (as mentioned above) | 20 parts |
| Sucrose | 5 parts |
| Clay | 5 parts |

The above components were uniformly mixed and pulverized, and while adding a small amount of water, the mixture was mixed and stirred for granulation, followed by drying to obtain a granular wettable powder.

| EXAMPLE 5 Granular wettable powder | |
|---|---|
| Compound No. 2 | 10 parts |
| Ammonium chloride | 60 parts |
| Liquid paraffin (High White 70, trademark, manufactured by Nippon Petrochemicals Co., Ltd., dynamic viscosity at 40° C.: 13 cSt) | 10 parts |
| Polyoxyethylene alkylaryl ether sulfate (Dickssol WK, trademark, manufactured by Daiichi Kogyo K.K.) | 5 parts |
| Fine silica powder (as mentioned above) | 10 parts |
| Sucrose | 5 parts |

The above components were uniformly mixed and pulverized, and while adding a small amount of water, the mixture was mixed and stirred for granulation, followed by drying to obtain a granular wettable powder.

| EXAMPLE 6 Wettable powder | |
|---|---|
| Compound No. 3 | 5 parts |
| Ammonium sulfate | 40 parts |
| Condensation product of sodium naphthalene sulfonate (as mentioned above) | 5 parts |
| Fine silica powder (as mentioned above) | 5 parts |
| Clay | 45 parts |

The above components were uniformly mixed and then pulverized to obtain a wettable powder.

| EXAMPLE 7 Wettable powder | |
|---|---|
| Compound No. 16 | 5 parts |
| Urea | 70 parts |
| Condensation product of sodium naphthalene | 5 parts |

EXAMPLE 7 Wettable powder (continued)

| | |
|---|---|
| sulfonate (as mentioned above) | |
| Fine silica powder (as mentioned above) | 5 parts |
| Clay | 15 parts |

The above components were uniformly mixed and then pulverized to obtain a wettable powder.

EXAMPLE 8 Wettable powder

| | |
|---|---|
| Compound No. 20 | 5 parts |
| Urea | 60 parts |
| Soybean oil (dynamic viscosity at 40° C.: 18 cSt) | 10 parts |
| Polyoxyethylene tridecyl ether (Pegnol T-8, trademark, manufactured by Toho Chemical Co., Ltd., average addition molarity of ethylene oxide: 8) | 3 parts |
| Condensation product of sodium naphthalene sulfonate (as mentioned above) | 5 parts |
| Fine silica powder (as mentioned above) | 10 parts |
| Clay | 7 parts |

The above components were uniformly mixed and then pulverized to obtain a wettable powder.

EXAMPLE 9 Flowable

| | |
|---|---|
| Compound No. 22 | 10 parts |
| Ammonium chloride | 5 parts |
| Condensation product of sodium naphthalene sulfonate (as mentioned above) | 5 parts |
| Ethylene glycol | 10 parts |
| Xanthane gum | 0.1 part |
| Water | 69.9 parts |

The above components were uniformly mixed and then pulverized to obtain a flowable.

EXAMPLE 10 Flowable

| | |
|---|---|
| Compound No. 22 | 10 parts |
| Ammonium chloride | 5 parts |
| Polyoxyethylene myristyl ether (Pegnol M-10, manufactured by Toho Chemical Co., Ltd., average addition molarity of ethylene oxide: 10) | 5 parts |
| Condensation product of sodium naphthalene sulfonate (as mentioned above) | 5 parts |
| Ethylene glycol | 10 parts |
| Xanthane gum | 0.1 part |
| Water | 64.9 parts |

The above components were uniformly mixed and then pulverized to obtain a flowable.

EXAMPLE 11 Dust

| | |
|---|---|
| Compound No. 17 | 0.2 part |
| Urea | 5 parts |
| Flocculating agent (Driless A, trademark, Sankyo Co., Ltd.) | 1 part |
| Fine silica powder (as mentioned above) | 1 part |
| DL clay | 92.8 parts |

The above components were uniformly mixed and then pulverized to obtain DL dust.

EXAMPLE 12 Dust

| | |
|---|---|
| Compound No. 17 | 0.2 part |
| Urea | 5 parts |
| Liquid paraffin (High White 120, trademark, manufactured by Nippon Petrochemicals Co., Ltd., dynamic viscosity at 40° C.: 34 cSt) | 0.5 part |
| Flocculating agent (Driless A, trademark, manufactured by Sankyo Co., Ltd.) | 1 part |
| Fine silica powder (as mentioned above) | 1 part |
| DL clay | 92.3 parts |

The above components were uniformly mixed and then pulverized to obtain DL dust.

EXAMPLE 13 Dust

| | |
|---|---|
| Compound No. 20 | 0.1 part |
| Urea | 5 parts |
| Rapeseed oil (dynamic viscosity at 40° C.: 15 cSt) | 2 parts |
| Flocculating agent (Driless A, trademark, manufactured by Sankyo Co., Ltd.) | 1 part |
| Fine silica powder (as mentioned above) | 3 parts |
| DL clay | 88.9 parts |

The above components were uniformly mixed and then pulverized to obtain DL dust.

EXAMPLE 14 Dust

| | |
|---|---|
| Compound No. 21 | 0.1 part |
| Urea | 5 parts |
| Polyoxyethylene tridecyl ether (as mentioned above) | 0.2 part |
| Flocculating agent (Driless A, trademark, manufactured by Sankyo Co., Ltd.) | 1 part |
| Fine silica powder (as mentioned above) | 1 part |
| DL clay | 92.7 parts |

The above components were uniformly mixed and then pulverized to obtain DL dust.

EXAMPLE 15 Dust

| | |
|---|---|
| Compound No. 1 | 0.1 part |
| Tricyclazole | 1 part |
| Urea | 5 parts |
| Rice bran oil (dynamic viscosity at 40° C.: 8 cSt) | 2 parts |
| Flocculating agent (Driless A, trademark, manufactured by Sankyo Co., Ltd.) | 1 part |
| Fine silica powder (as mentioned above) | 3 parts |
| DL clay | 87.9 parts |

The above components were uniformly mixed and then pulverized to obtain DL dust.

Now, Formulation Examples used for comparative purposes in the following tests, will be shown.

COMPARATIVE EXAMPLE 1 Granular wettable powder

10 Parts of Compound No. 1, 5 parts of the condensation product of sodium naphthalene sulfonate (as mentioned above), 5 parts of fine silica powder (as mentioned above), 5 parts of sucrose and 75 parts of clay were uniformly mixed and pulverized, and while adding a small amount of water, the mixture was mixed and stirred for granulation, followed by drying to obtain a granular wettable powder.

COMPARATIVE EXAMPLE 2 Granular wettable powder

10 Parts of Compound No. 1, 70 parts of potassium chloride, 5 parts of the condensation product of sodium naphthalene sulfonate (as mentioned above), 5 parts of fine silica powder (as mentioned above), 5 parts of sucrose and 5 parts of clay were uniformly mixed and pulverized, and while adding a small amount of water, the mixture was mixed and stirred for granulation, followed by drying to obtain a granular wettable powder.

COMPARATIVE EXAMPLE 3 Granular wettable powder

10 Parts of Compound No. 1, 70 parts of calcium phosphate, 5 parts of the condensation product of sodium naphthalene sulfonate (as mentioned above), 5 parts of fine silica powder (as mentioned above), 5 parts of sucrose and 5 parts of clay were uniformly mixed and pulverized, and while adding a small amount of water, the mixture was mixed and stirred for granulation, followed by drying to obtain a granular wettable powder.

COMPARATIVE EXAMPLE 4 Granular wettable powder

10 Parts of Compound No. 1, 10 parts of polyoxyethylene lauryl ether (as mentioned above), 5 parts of the condensation product of sodium naphthalene sulfonate (as mentioned above), 10 parts of fine silica powder (as mentioned above), 5 parts of sucrose and 60 parts of clay were uniformly mixed and pulverized, and while adding a small amount of water, the mixture was mixed and stirred for granulation, followed by drying to obtain a granular wettable powder.

COMPARATIVE EXAMPLE 5 Granular wettable powder

10 Parts of Compound No. 2, 10 parts of liquid paraffin (High White 70, trademark, as mentioned above), 5 parts of polyoxyethylene alkylaryl ether sulfate (as mentioned above), 10 parts of fine silica powder (as mentioned above), 5 parts of sucrose and 60 parts of clay were uniformly mixed and pulverized, and while adding a small amount of water, the mixture was mixed and stirred for granulation, followed by drying to obtain a granular wettable powder.

COMPARATIVE EXAMPLE 6 Wettable powder

5 Parts of Compound No. 20, 10 parts of soybean oil (as mentioned above), 3 parts of polyoxyethylene tridecyl ether (as mentioned above), 5 parts of the condensation product of sodium naphthalene sulfonate (as mentioned above), 10 parts of fine silica powder (as mentioned above) and 67 parts of clay were uniformly mixed and then pulverized to obtain a wettable powder.

COMPARATIVE EXAMPLE 7 DL dust 0.1 Part of Compound No. 20, 2 parts of rapeseed oil (as mentioned above), 1 part of the flocculating agent (Driless A, trademark, manufactured by Sankyo Co., Ltd.), 3 parts of fine silica powder (as mentioned above) and 93.9 parts of DL-clay were uniformly mixed and then pulverized to obtain DL dust.

COMPARATIVE EXAMPLE 8 DL dust 0.1 Part of Compound No. 21, 0.2 part of polyoxyethylene tridecyl ether (as mentioned above), 1 part of the flocculating agent (Driless A, trademark, manufactured by Sankyo Co., Ltd.), 1 part of fine silica powder (as mentioned above) and 97.7 parts of DL-clay were uniformly mixed and then pulverized to obtain DL dust.

TEST EXAMPLE 1 Growth control test on lawn

A granular wettable powder or a wettable powder prepared in accordance with each Example was diluted with water so that the dose of the cyclohexane derivative or its salt would be 250 g/ha and the amount of water applied would be 1000 l/ha, and applied to the foliages of bent grass (variety: Seaside) and wild grass cut to a height of 2 cm. The investigation was carried out by measuring the length of the foliages upon expiration of four weeks and eight weeks after the application, and the control rate was calculated in accordance with the following formula. The control rate was represented by an integer by rounding the calculated value to the nearest whole number. The results are shown in Table 5.

Control rate (%) =

$$\left(1 - \frac{\text{Elongation of the foliage in treated area}}{\text{Elongation of the foliage in non-treated area}}\right) \times 100$$

TABLE 5

| | Control rate (%) | | | |
|---|---|---|---|---|
| | Bent grass | | Lawn grass | |
| Reagent | 4 weeks after | 8 weeks after | 4 weeks after | 8 weeks after |
| Example 1 | 33 | 30 | 38 | 39 |
| Example 2 | 44 | 42 | 49 | 52 |
| Example 3 | 48 | 47 | 51 | 54 |
| Example 4 | 50 | 50 | 55 | 58 |
| Example 5 | 38 | 34 | 45 | 41 |
| Example 7 | 34 | 37 | 40 | 42 |
| Comparative Example 1 | 30 | 7 | 40 | 22 |
| Comparative Example 2 | 32 | 10 | 37 | 18 |
| Comparative Example 3 | 30 | 8 | 38 | 20 |
| Comparative Example 4 | 38 | 12 | 40 | 21 |
| Comparative Example 5 | 37 | 14 | 42 | 17 |
| Comparative Example 6 | 32 | 8 | 38 | 14 |

TEST EXAMPLE 2 Growth control test on rice plant

A dust prepared in accordance with each Example was applied to a rice plant (variety: Kinmaze) of the second leaf stage, so that the dose of the cyclohexane derivative or its salt would be 30 g/ha. The investigation was carried out by measuring the length of the foliage upon expiration of two weeks and four weeks after the application, and the control rate was calculated in accordance with the formula in Test Example 1. The control rate was represented by an integer by rounding the calculated value to the nearest whole number. The results are shown in Table 6.

TABLE 6

| | Control rate (%) | |
|---|---|---|
| Reagent | 2 weeks after | 4 weeks after |
| Example 11 | 45 | 45 |
| Example 12 | 52 | 54 |
| Example 13 | 55 | 58 |
| Example 15 | 43 | 48 |
| Comparative Example 7 | 43 | 15 |
| Comparative Example 8 | 45 | 13 |

TEST EXAMPLE 3 Growth control test on wheat

A granular wettable powder prepared in accordance with Example 1 was diluted with water so that the dose of the cyclohexane derivative or its salt would be 500 g/ha and the amount of water applied would be 250 l/ha, and applied to wheat (variety: AVARON) of a third leaf stage. The investigation was carried out by measuring the length of the foliage upon expiration of two weeks and four weeks after the application, and the control rate was calculated in accordance with the formula in Test Example 1. The growth control rate was represented by an integer by rounding the calculated value to the nearest whole number. The results are shown in Table 7.

TABLE 7

| Test compound | Control rate (%) 2 weeks after | 4 weeks after |
|---|---|---|
| Compound 1  | 45 | 46 |
| Compound 4  | 36 | 37 |
| Compound 5  | 28 | 25 |
| Compound 6  | 32 | 35 |
| Compound 7  | 48 | 50 |
| Compound 8  | 40 | 38 |
| Compound 9  | 30 | 29 |
| Compound 10 | 33 | 35 |
| Compound 11 | 35 | 35 |
| Compound 12 | 37 | 35 |
| Compound 13 | 35 | 33 |
| Compound 14 | 38 | 37 |
| Compound 15 | 40 | 44 |
| Compound 18 | 33 | 36 |
| Compound 19 | 35 | 32 |
| Compound 20 | 52 | 54 |

With the plant growth regulator composition of the present invention comprising the cyclohexane derivative or its salt and the nitrogen-containing water-soluble inorganic substance or urea, the effects last for a long period of time at a low dose, and a high plant growth regulating activity can be obtained, whereby it is unnecessary to apply the agricultural chemical excessively, and thus it is free from a problem such as an environmental pollution or a danger to the safety of animals and human being. Further, such effects can be increased by incorporating a polyoxyethylene alkyl ether, a polyoxyethylene alkylphenyl ether, a mineral oil or a vegetable oil. Furthermore, the plant growth regulator composition of the present invention has a feature that the applicable period is wide, and it provides a constant effect irrespective of the temperature or the types of plant species. Further, it also has a feature that it is suitable for use in admixture with other agents.

We claim:

1. A plant growth regulator composition, comprising an effective amount of each of:

a) a cyclohexane compound of the formula:

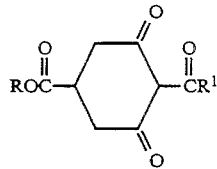

wherein R is hydrogen, lower alkyl, lower alkylthioalkyl, unsubstituted phenyl or phenyl substituted by halogen, lower alkyl or lower alkoxy; and $R^1$ is lower cycloalkyl, lower alkyl, unsubstituted benzyl or benzyl substituted by halogen, lower alkyl or lower alkoxy; phenylethyl, phenoxymethyl, 2-thienylmethyl, lower alkoxymethyl, lower alkylthiomethyl or a salt thereof;

b) a nitrogen-containing water-soluble substance selected from the group consisting of ammonium sulfate, ammonium nitrate, ammonium chloride, ammonium phosphate, sodium nitrate, potassium nitrate and urea; and c) one or more substances selected from the group consisting of polyoxyethylene alkyl ethers, polyoxyethylene alkylphenyl ethers, mineral oils and vegetable oils.

2. The plant growth regulator composition of claim 1, wherein the nitrogen-containing water-soluble inorganic substance or urea is in an amount of from 0.5 to 100 parts by weight per part by weight of the cyclohexane derivative or a salt thereof.

3. The plant growth regulator composition of claim 1, wherein an average addition molarity of ethylene oxide in the polyoxyethylene alkyl ethers and polyoxyethylene-alkylphenyl ethers is from 2 to 16 moles, and a carbon number of the alkyl group is from 8 to 16.

4. The plant growth regulator composition of claim 1, wherein said mineral oils or the vegetable oils each have a dynamic viscosity of from 1 to 300 cSt. at 40° C.

5. The plant growth regulator composition according to claim 1, which comprises an ethyl ester of 3,5-dioxo-4propionylcyclohexane carboxylic acid or a calcium salt of 3,5-dioxo-4-propionylcyclohexane carboxylic acid, a polyoxyethylene alkyl ether or a polyoxyethylene alkylphenyl ether in which the average addition molarity of ethylene oxide is from 2 to 16 mole and the carbon number of alkyl groups is from 8 to 16, and ammonium sulfate.

6. The plant growth regulator composition of claim 1, wherein a weight ratio of the ester or salt of the cyclohexane carboxylic acid, the ammonium sulfate and the polyoxyethylene alkyl ether or the polyoxyethylene alkylphenyl ether is 1:0.5/100:0.5–20.

7. The plant growth regulator composition of claim 1, which is of the formula (I) and which is selected from the group consisting of compounds where $R^2$ is methyl, $R^3$ is methyl and M is $H_2N^+(C_2H_4OH)_2$, $R^2$ is ethyl $R^3$ is methyl and M is $H_2N+(C_2H_4OH)_2$; and $R^2$ is ethyl, $R^3$ is ethyl and M is $H_2N+(C_2H_4OH)_2$.

8. The plant growth regulator composition of claim 1, which is of the formula (II) and which is selected from the group consisting of compounds where $R^3$ is propyl and M is $HN^+(C_2H_5)_3$, $R_3$ is ethyl and M is

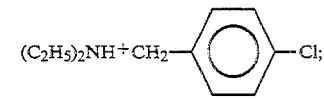

and $R^3$ is ethyl and M is $Na^+$.

9. A plant growth regulator composition, comprising an effective amount of each of:

a) a cyclohexane compound of the formula:

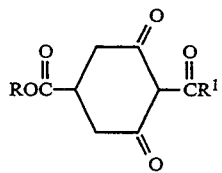

wherein R is hydrogen, lower alkyl, lower alkylthioalkyl, unsubstituted phenyl or phenyl substituted by halogen, lower alkyl or lower alkoxy; and $R^1$ is lower cycloalkyl, unsubstituted benzyl or benzyl substituted by halogen, lower alkyl or lower alkoxy; phenylethyl, phenoxymethyl, 2-thienylmethyl, lower alkoxymethyl, lower alkylthiomethyl or a salt thereof;

b) a nitrogen-containing water-soluble substance selected from the group consisting of ammonium sulfate, ammonium nitrate, ammonium chloride, ammonium phosphate, sodium nitrate, potassium nitrate and urea; and c) one or more substances selected from the group consisting of polyoxyethylene alkyl ethers, polyoxyethylene alkylphenyl ethers, mineral oils and vegetable oils.

* * * * *